United States Patent [19]
Clement et al.

[11] Patent Number: 5,421,824
[45] Date of Patent: Jun. 6, 1995

[54] BLADDER EVACUATOR

[75] Inventors: Thomas P. Clement, Bloomington, Ind.; Robert A. Roth, Brookline, Mass.

[73] Assignee: Boston Scientific Corporation, Watertown, Mass.

[21] Appl. No.: 276,350

[22] Filed: Jul. 18, 1994

Related U.S. Application Data

[63] Continuation of Ser. No. 856,599, Mar. 24, 1992, abandoned, which is a continuation of Ser. No. 416,808, Oct. 3, 1989, abandoned, which is a continuation-in-part of Ser. No. 154,192, Feb. 10, 1988, abandoned.

[51] Int. Cl.⁶ ............................................ A61M 1/00
[52] U.S. Cl. .................................... 604/29; 222/211; 128/760; 128/898; 604/190; 604/212; 604/36; 604/37; 604/73
[58] Field of Search ............... 604/75, 190, 212, 213, 604/331, 22, 43, 35-37, 28, 29, 73; 128/898, 760, 766, 768; 222/189.211, 215

[56] References Cited

U.S. PATENT DOCUMENTS 764,996   7/1904  Ellis .
873,728  12/1907  Crisenberry .
877,926   2/1908  Hilker .
1,484,621  2/1924  Bond et al. .
1,627,941  5/1927  Wappler .
1,925,230  9/1933  Buckhout .
3,471,064 10/1969  Micallef .
3,785,380  1/1974  Brumfield .
3,831,605  8/1974  Fournier .
3,892,226  7/1975  Rosen .
3,908,660  9/1975  Kaplan .
4,221,225  9/1980  Sloan .
4,264,577  4/1981  Zimmerman et al. .
4,360,013 11/1982  Barrows .
4,564,362  1/1986  Burnhill .
4,787,889 11/1988  Steppe et al. .
4,801,292  1/1989  Watson .
4,806,101  2/1989  Rossi .
4,880,408 11/1989  Cumes et al. .

FOREIGN PATENT DOCUMENTS 2136690  9/1984  United Kingdom .

Primary Examiner—Randall L. Green
Assistant Examiner—Rob Clarke
Attorney, Agent, or Firm—Lerner, David, Littenberg, Krumholz & Mentlik

[57] ABSTRACT

A method of irrigation of a cavity of a human body by means of a medical device consisting of a container for a fluid and a filter. The container is formed with an open neck and a peripheral wall defining the receiving volume. A portion of the peripheral wall at the open neck is squeezable. The filter consists of an elongated filter element situated at an open neck of the container adjacent the squeezable portion and extending within the fluid receiving volume. The method comprises the steps of applying compressional forces to the squeezable portion of the container to urge the fluid from the fluid receiving volume into the body cavity; releasing the compressional forces to allow the squeezable portion to expand and to withdraw the fluid from the body cavity into the fluid receiving volume; and repeating the above steps.

11 Claims, 2 Drawing Sheets

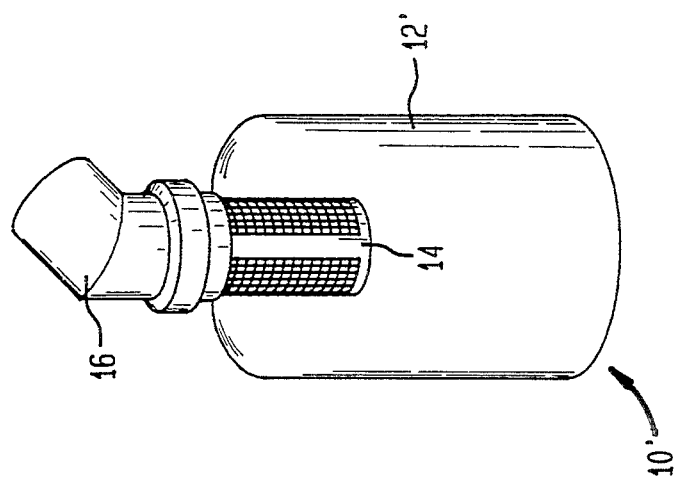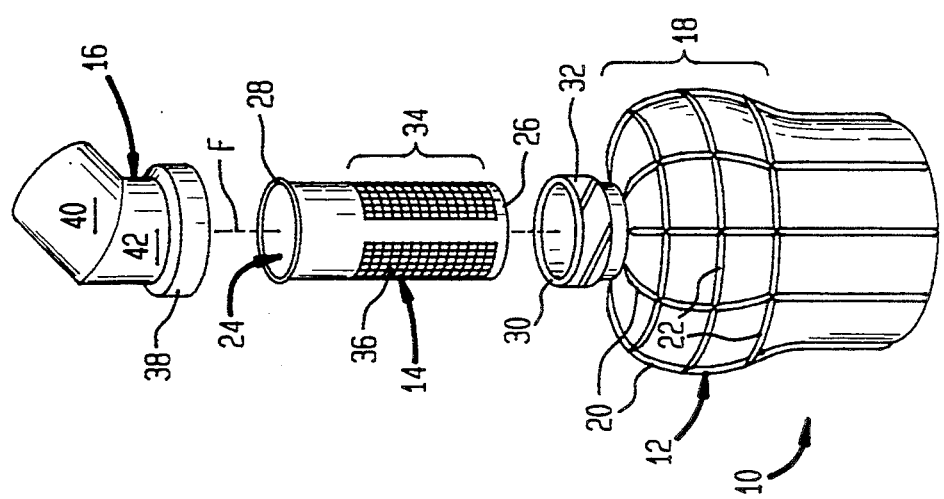

BLADDER EVACUATOR

This is a continuation of patent application Ser. No. 07/856,599 filed Mar. 24, 1992 presently abandoned which is a continuation of Ser. No. 07/416,808 filed Oct. 3, 1989 presently abandoned, which is a continuation-in-part of Ser. No. 07/154,192 filed Feb. 10, 1988 presently abandoned.

BACKGROUND OF THE INVENTION

The invention relates to an evacuator device for allowing a volume of fluid to be repeatedly forced into and withdrawn from a passageway of the body.

For example, in the field of urological surgery, the need frequently arises to evacuate by flushing, pieces of solid or semi-solid material from the urinary tract, e.g., the bladder. Devices in the past have removed particles, such as stones, blood clots, pieces of tissue and the like by first introducing a sterile fluid such as saline solution into a body cavity and thereafter withdrawing the fluid to flush the particles frog the body. The mixture is collected in a chamber and must be strained or filtered before the fluid is recirculated into the body cavity for collection of further particles. One particular application is flushing free-floating prostatic tissue chips from the bladder following a transurethral resectioning (TUR) procedure.

SUMMARY OF THE INVENTION

According to the invention, a medical irrigation device for alternately introducing fluid into and withdrawing fluid from a body cavity through a conduit comprises a container for fluid defining a fluid-receiving volume and having an open neck, filter means disposed within the volume of the container for separation of tissue particles above a predetermined size from fluid introduced from the volume through the open neck, and cap means for interconnecting the open neck and the conduit.

In the improved medical irrigation device of the invention, the filter means comprises an elongated filter element disposed adjacent the open neck and extending within the volume of the container, the filter element being disposed about an axis and defining a filter opening axially aligned with and spaced from the open neck. The device is adapted-for application of compressional forces upon the container in directions generally transverse to the axis of the filter element for urging fluid within the volume of the container toward and through the filter element substantially free of tissue particles in excess of the predetermined size, to pass through the open neck into the conduit toward the body cavity, and upon release of the compressional forces, the container is adapted to expand to withdraw unfiltered tissue-particle-bearing fluid into the volume of the container via the open neck and generally axially within the filter element through the filter opening.

Preferred embodiments of the invention may include one or more of the following features. The container comprises a generally cylindrical body portion. The filter element is generally cylindrical. The side walls of the container and filter element are substantially parallel. The container is comprised of resilient (e.g., polymeric) material such as polyvinyl chloride (PVC), polyethylene or polyproplylene. The cap comprises a first portion extending from the open neck and a second portion more adjacent to the conduit, the axes of the first and second portions defining an acute angle, e.g., of the order of about 45°. The filter element comprises a mesh having filter pore openings of the order of about 1 mm or less, preferably about 0.5 to 1.0 mm. The conduit comprises a working channel of an endoscope.

According to another aspect of the invention, a method for irrigation of a body cavity for flushing particles of tissue therefrom by alternately introducing fluid into and withdrawing fluid from the cavity through a conduit comprises the steps of introducing the distal end of a conduit-defining instrument into a body cavity to be irrigated, connecting the proximal end of the conduit to a medical irrigation device, e.g., as described above, applying compressional forces upon the container in directions transverse to the filter axis to urge fluid within the volume of the container toward and through the filter element substantially free of tissue particles in excess of the predetermined size passing the open neck and into the conduit toward the body cavity, releasing the Compressional forces to allow the container to expand to withdraw unfiltered tissue-particle-bearing fluid into the volume via the open neck and generally axially within the filter element through the filter opening, and repeating alternately the steps of applying and releasing compressional forces upon the container to repeatedly introduce substantially tissue-particle-free fluid into the body cavity and withdraw tissue-particle-bearing fluid from the body cavity, the medical irrigation device efficiently separating tissue particles above the predetermined size from the fluid introduced into the body cavity upon each application of compressional force.

In preferred embodiments of the method, the conduit-defining instrument comprises an endoscope and the conduit is the working channel of the endoscope, and the method comprises positioning the distal end of the endoscope and observing flushing of tissue particles via the endoscope viewing channel. Also, the container expands resiliently upon release of compressional forces to withdraw fluid from the body cavity.

Other advantages and features of the invention will be apparent from the following description of a presently preferred embodiment, and from the claims.

DESCRIPTION OF THE PREFERRED EMBODIMENTS

We first briefly describe the Figures.

DRAWINGS

Figure 4:
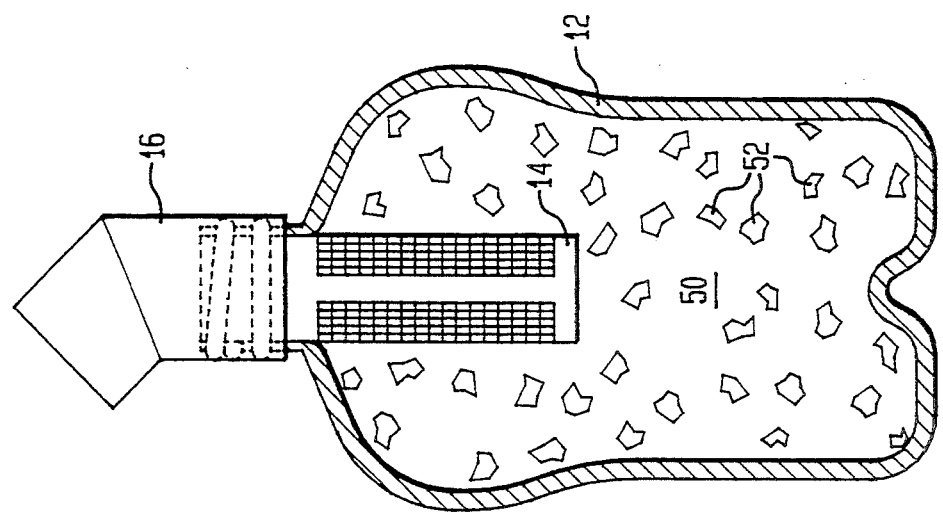
Figure 3:
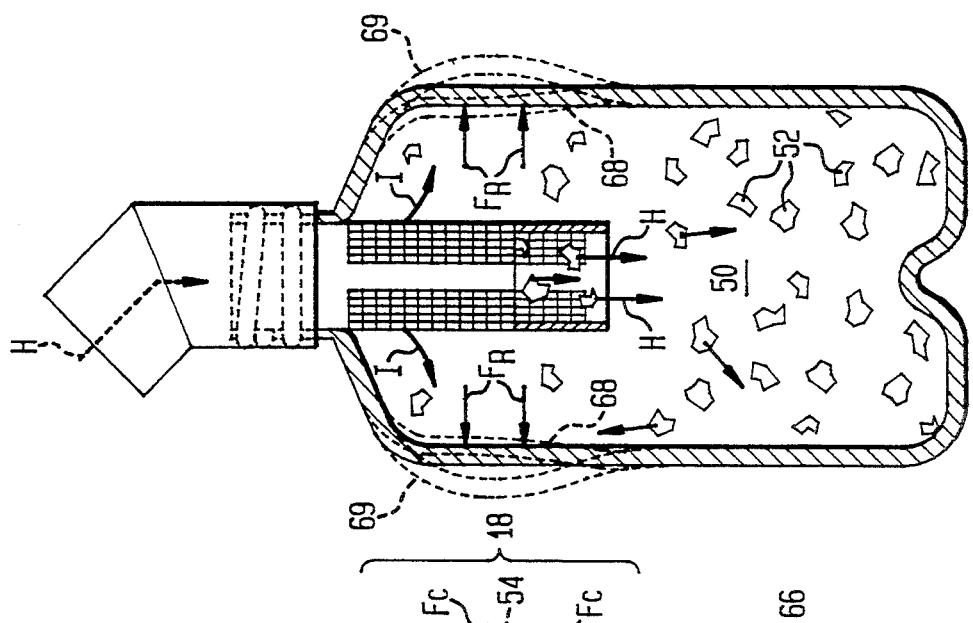
Figure 2:
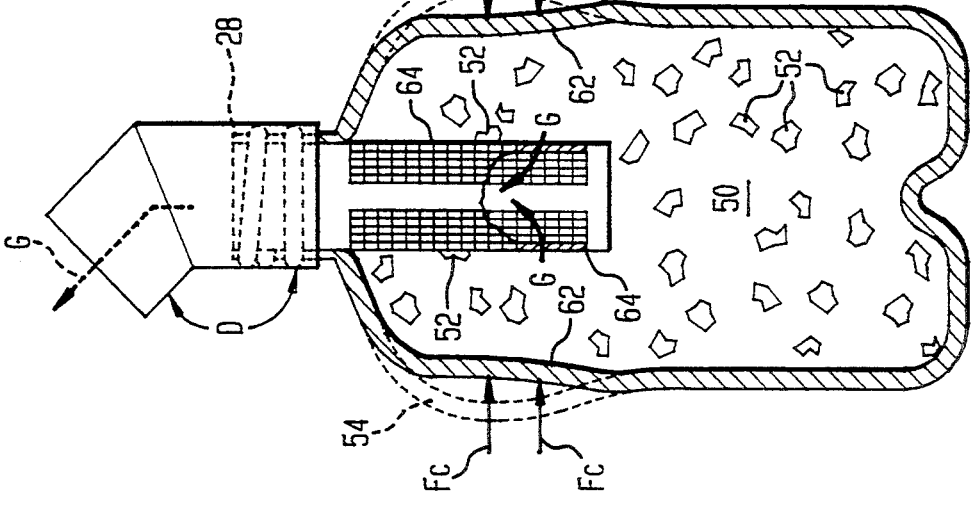

FIG. 1 is an exploded perspective view of a bladder evacuator of the invention;

FIGS. 2, 3, and 4 are side views, partially in section, of the bladder evacuator, FIG. 2 showing application of transverse compressional forces for introduction of essentially tissue-particle-free fluid into a body, FIG. 3 showing release of compressional forces to allow tissue-particle-bearing fluid to be withdrawn from the body, and FIG. 4 showing the bladder evacuator briefly between release and re-application of compressional forces; and FIG. 5 is a perspective view of an alternate embodiment of the evacuator.

Referring to FIG. 1, a bladder evacuator 10 of the invention for quickly and efficiently removing particles from a body cavity, e.g., prostatic tissue chips after a transurethral resectioning (TUR) procedure, consists of a squeezable, flexible container 12, a filter element 14 extending within container 12, and a connector 16.

Container 12 is generally cylindrical and is sized to hold about 12 ounces of irrigation fluid. Preferably, the container is formed of resilient material, e.g., polyvinyl chloride (PVC), polyethylene or polypropylene, with a wall thickness of about 0.156 inch, and is transparent to allow the user to monitor the fluid. At least the upper segment 18 of the container consists a squeezable, ribbed portion, preferably disposed generally coaxially with the longitudinal axis F of filter element 14. Vertical and horizontal ribs 20, 22 along the exterior surface of container 12 provide increased resiliency.

Filter element 14 consists of a molded plastic cylinder open at the top 24 and having a filter opening 26 at the bottom. A flange 28 about the perimeter of the top opening is sized to rest on the top lip 30 of the neck 32 of the container 12. Filter 14 includes a screen area 34 extending generally about its circumference and along its length, having pores 36 sized to restrict throughflow of tissue chips and other particles above a predetermined size, e.g., pores 36 are approximately 0.5 to 1.0 millimeter square.

Connector 16, e.g. also of plastic, has a threaded base 38 for threading onto neck 32 of container 12 and engages upon flange 28 to hold filter 14 in place. Connector 16 has upper and lower portions 40, 42 disposed at angle D (FIG. 2), e.g., about 45°, for connection to a working channel of an endoscope (not shown).

The container 12 (FIG. 1) of the bladder evacuator 10 is filled with an irrigation fluid, e.g., saline solution, and assembled with the filter element 14 and connector 16. An endoscope is advanced to the surgical site as the physician observes through the viewing channel of the endoscope. Connector 16 is connected to the working channel of the endoscope to provide a conduit for fluid from the container to the site.

Referring now to FIG. 2, the bladder evacuator 10 is shown during a flushing procedure, and contains fluid 50 and numerous chip 52 of tissue removed from the body. Compressional forces (arrows $F_c$) of at least a minimum magnitude, e.g., 2 to 4 lbs., are applied to upper portion 18 of container 12 to displace the container walls 54 in region 18 from their initial dashed line position inwardly, toward axis F of filter element 14, to cause the irrigation fluid 50 to flow toward the filter and through the filter pores 36. The pores 36 are sized to restrict through-flow of tissue chips 52 above a predetermined size, and application of the compressional forces $F_c$ upon portion 18 of the container causes substantially only the fluid within the upper portion 18 of the container, between the container wall 64 and the filter surface 62 to flow directly toward the filter surface; fluid in the lower portion 66 of the container is essentially undisturbed. The fluid (arrows G) passes through the filter pores (leaving tissue chips 52 behind) and through the top opening 24 of the filter, out the open neck of the container and thereafter from opening 26 of connector 16 into the working channel of the endoscope, and therethrough into the bladder of a patient.

Referring now to FIG. 3, after the walls 54 of the upper portion 18 of the container 12 are compressed to their innermost position adjacent the surface 64 of the filter element (indicated by dashed lines 68), the compressional forces ($F_c$, FIG. 2) are released, and the resilient forces of the container (arrows $F_R$) cause the container walls to move outwardly, toward their original positions (dashed lines 69). The bladder evacuator and conduit are a closed system, and movement of the walls acts to withdraw the flushing fluid from within the body, carrying with it tissue chips removed in surgery. The tissue-carrying fluid enters the evacuator 10 via the connector 16 to flow along the axis F of the filter, and into the container 12 through the filter opening 26 of filter element 14. (The direction and force of flow (arrows H) into the container serves to sweep a substantial portion of the tissue chips 52 from within the filter element 14, even as a small portion (arrows I) of the fluid is drawn through the pores 36 of the surface 64 of the filter.

Referring now to FIG. 4, after release, (FIG. 3) and immediately before reapplication of compressional forces (FIG. 2), the container 12 is full of tissue-chip bearing fluid, typically in random movement. A short pause between cycles allows some settling of tissue-chips 52, e.g., from within the volume of the filter element 14, but little, or no delay if desired, is necessary before the fluid is again forced through the pores 36 of filter 14, and the returning irrigation fluid is substantially free of tissue chips and particles above the predetermined size.

The irrigation procedure can thus be carried out quickly, with little delay required between flushing strokes, and with little backflow of tissue particles into the body.

Other embodiments are within the scope of the following claims. For example, bladder evacuator 10' may have a container 12' in the form of a right cylinder (FIG. 5).

What is claimed is:

1. A method of irrigation of a cavity of a human body and flushing particles of tissue therefrom by means of a medical irrigation device, comprising a container for a fluid having an open neck and a peripheral wall defining a fluid-receiving volume, at least a portion of said peripheral wall at said open neck being squeezable, filter means disposed within the fluid-receiving volume for separation of said tissue particles above a predetermined size, interconnecting cap means for interconnecting said open neck to a conduit, said filter means comprising an elongated filter element situated at said open neck adjacent to said squeezable portion and extending within said fluid-receiving volume, said filter element being disposed about a longitudinal axis of the container and defining a filter opening axially aligned with said open neck;

said method comprising the steps of:
(a) applying compressional forces to said squeezable portion of said container in the direction transverse to said longitudinal axis to urge said fluid from said fluid-receiving volume toward and through said filter element, said open neck and the conduit into said body cavity, so that said fluid in a substantially tissue-particle-free condition is delivered to said cavity;
(b) releasing said compressional forces to allow at least said squeezable portion of the container to expand and to withdraw said fluid in an unfiltered tissue-particle-bearing condition from said body cavity into said fluid-receiving volume through said conduit, said open neck and generally axially through the filter opening; and
(c) repeating the steps "a" and "b" to repeatedly introduce said fluid in the substantially tissue-particle-free condition into the body cavity and to withdraw said fluid in the tissue-particle-bearing condition from the body cavity into the receiving volume of the container.

2. The method of claim 1, wherein said squeezable portion of said peripheral wall is substantially axially aligned with said filter element and in the step "a" applying of said compressional forces to said squeezable portion of the container causes substantially only the fluid within the part of the container adjacent said open neck to flow directly toward the filter element.

3. The method of claim 2, wherein said fluid in a lower portion of the container is essentially undisturbed.

4. The method of claim 3, wherein said medical irrigation device further comprises an endoscope assembly having a working channel and a viewing device adapted to be received within said working channel, said conduit forming said working channel of said endoscope assembly, whereby said method further comprises the steps of positioning of said working channel of the endoscope assembly into said body cavity and observing an interior of said cavity through said viewing device situated within said working channel.

5. A method of irrigation of a human bladder and flushing particles of tissue therefrom by means of a medical irrigation device connected to an endoscope assembly having at least a working channel, said medical irrigation device, comprising a container for a fluid having an open neck and a peripheral wall defining a fluid-receiving volume, at least a portion of said peripheral wall at said open neck and said filter element being squeezable, filter means disposed within said fluid-receiving volume for separation of said tissue particles above a predetermined size, cap interconnecting means for interconnecting said open neck to said working channel of the endoscope, said filter means comprising an elongated filter element disposed at the open neck adjacent to said squeezable portion and extending within said fluid-receiving volume, the filter element being disposed about a longitudinal axis of the container and defining a filter opening axially aligned with and spaced from said open neck;

said method comprising the steps of:
(a) positioning of said working channel of the endoscope within the human bladder;
(b) applying compressional forces to said squeezable portion of the container in the direction transverse to said longitudinal axis to urge said fluid from said fluid-receiving volume toward and through said filter element, said open neck and the working channel of the endoscope into the bladder, so that said fluid in a substantially tissue-particle-free condition being delivered to the bladder; and
(c) releasing said compressional forces to allow at least said squeezable portion of said container to expand and withdraw said fluid in an unfiltered tissue-particle-bearing condition from said bladder into said fluid-receiving volume through said working channel, open neck and generally axially within the filter element through the filter opening.

6. The method of claim 5, further comprising repeating the steps "b" and "c" to repeatedly introduce the substantially tissue-particles-free fluid into the bladder and withdraw said tissue-particle-bearing fluid from the bladder.

7. The method of claim 6, wherein said squeezable portion of said peripheral wall is substantially axially aligned with said filter element and in the step "b" applying of said compressional forces to said squeezable portion of the container causes substantially only the fluid within the part of the container adjacent said open neck to flow directly toward the filter element and said fluid in a lower portion of the container is substantially undisturbed.

8. The method of claim 5 wherein said endoscope assembly further includes a viewing device adapted to be received within said working channel, whereby said method further comprises the step of observing an interior of said bladder through said viewing device situated within said working channel.

9. A method of irrigation of a cavity of a human body and flushing particles of tissue therefrom by means of medical irrigation device, comprising a container for a fluid having an open neck and a peripheral wall defining a fluid receiving volume, said open neck being connected to a conduit, filter means disposed within the fluid receiving volume for separation of said tissue particles above a predetermined size, said filter means comprising an elongated filter element situated at said open neck and extending within said fluid-receiving volume, said elongated filter element being disposed about a longitudinal axis of the container and defining a filter opening axially aligned with said open neck, at least a portion of said peripheral wall at said open neck and said filter element being squeezable, said squeezable portion being substantially axially aligned with said filter element;

said method comprising the steps of:
(a) applying compressional forces to said squeezable portion of the container in the direction transverse to said longitudinal axis so as to cause said fluid substantially within the part of the container adjacent said filter element to flow toward and through said filter element, said open neck and the conduit into said body cavity, so that said fluid in a substantially tissue-particle-precondition is delivered to said cavity;
(b) releasing said compressional forces to allow at least said squeezable portion of the container to expand and to withdraw said fluid in an unfiltered tissue-particle-bearing condition from said body cavity into said fluid-receiving volume through said conduit, said open neck and generally axially through the filter opening; and
(c) repeating the steps "a" and "b" to repeatedly introduce said fluid in the substantially tissue-particle-free condition into the body cavity and to withdraw said fluid in the tissue-particle-bearing condition from the body cavity into the receiving volume of the container.

10. The method of claim 9, wherein in the step "a" said fluid in a lower portion of the container is essentially undisturbed.

11. The method of claim 10, wherein said medical irrigation device further comprises an endoscope assembly having a working channel and a viewing device adapted to be received within said working channel, said conduit forming said working channel of said endoscope assembly, whereby said method further comprises the steps of positioning of said working channel of the endoscope assembly into said body cavity and observing an interior of said cavity through said viewing device situated within said working channel.

* * * * *